United States Patent
Sossong

(10) Patent No.: US 6,719,714 B2
(45) Date of Patent: Apr. 13, 2004

(54) CLAW TOE STRAIGHTENING CLAMP

(76) Inventor: Charles E. Sossong, 325 Ontario St., Lockport, NY (US) 14094

( * ) Notice: Subject to any disclaimer, the term of this patent is extended or adjusted under 35 U.S.C. 154(b) by 115 days.

(21) Appl. No.: 10/116,270

(22) Filed: Apr. 3, 2002

(65) Prior Publication Data

US 2003/0191422 A1 Oct. 9, 2003

(51) Int. Cl.$^7$ ................................................. A61F 5/60
(52) U.S. Cl. ........................................ 602/30; 128/893
(58) Field of Search ................... 602/23, 30; 128/869, 128/845, 846, 877, 878, 879, 882, 893; 606/157, 158

(56) References Cited

U.S. PATENT DOCUMENTS

| | | | |
|---|---|---|---|
| 323,775 A | * | 8/1885 | Bender |
| 2,471,997 A | | 5/1949 | Baltor |
| 2,636,491 A | * | 4/1953 | La Bille |
| 2,949,112 A | | 8/1960 | Murray |
| 3,299,894 A | | 1/1967 | Charlebois |
| 3,429,309 A | | 2/1969 | Kurth et al. |
| 3,866,611 A | * | 2/1975 | Baumrucker ................ 128/885 |
| 5,653,128 A | | 8/1997 | Warren, Jr. et al. |
| D393,931 S | | 4/1998 | Rue |
| 5,957,871 A | * | 9/1999 | Darcey ........................ 602/12 |
| 6,183,431 B1 | * | 2/2001 | Gach ........................... 128/882 |
| 6,503,216 B1 | * | 1/2003 | Thibodo ....................... 602/21 |

\* cited by examiner

Primary Examiner—Michael A. Brown
(74) Attorney, Agent, or Firm—Gene Scott - Patent Law & Venture Group

(57) ABSTRACT

A pair of rigid clamping blocks, each with a length approximating the width of a human foot across the toes is applied wherein one side of each of the blocks engages a compressible pad, and the other side of the blocks provides a longitudinal groove in an outfacing surface. A clamping wrap engages the longitudinal grooves in the pair of blocks when the blocks are placed on opposing sides of the toes and the clamping wrap encircles them, for applying a compressive force to the blocks and the toes sandwiched therebetween.

5 Claims, 2 Drawing Sheets

CLAW TOE STRAIGHTENING CLAMP

BACKGROUND OF THE INVENTION

1. Field of the Invention

This invention relates generally to medical arts and clamping devices for immobilizing a part of the body, and more particularly to a toe clamp capable of applying a compressive force to the toes for the purpose of straightening them.

2. Description of Related Art

The following art defines the present state of this field:

Rue, U.S. Pat. No. Des. 393,931 describes a toe spacer device design

Baltor, U.S. Pat. No. 2,471,997 describes a toe brace comprising a member having ring portions adapted to receive the toes of a foot, said ring portions having curved outer and inner surfaces and being interconnected by webs at points of tangency between adjacent ring portions.

Murray, U.S. Pat. No. 2,949,112 describes a toe positioner comprising a resilient molded piece having a member which spans a plurality of the toes of the feet which member has reslient three dimensional form exactly conforming to the contours of the exposed surface portion of the toes, a plurality of interdigital elements carried by said member each of which is adapted to fit into a space between the toes, said interdigital elements being resilient and having a three dimensional form that of the toes adjacent the space whereby the toes are separated by resilient yielding member that apply pressure conforming to the natural contour of the toes and in which structure the said member that spans a plurality of the toes of the feet completely evenelops the front portion of the foot.

Charlebois, U.S. Pat. No. 3,299,894 describes a disposable foot appliance having a lower sole receiving member and a separately formed upper member secured thereto, said members comprising of a moisture absorbent soft paper tissue material, said upper member having an undulated front end portion and an uninterrupted foot receiving rear portion, a plurality of longituidinal extending loops and despressions in said upper member providing separate toe receiving compartments, said depressions extending from said undulated front end portion toward said rear end portion of said upper member and terminating therebetween to form webbed portions said webbed portions to be received in the area of the foot between each tow member to absorb excess moisture and means in said upper member to provide a circulation of air to the tow area.

Kurth et al., U.S. Pat. No. 3,429,309 describes a toe aeration appliance adapted to be mounted in partially toe-underlying and partially upwardly inserted relationship between toes of a foot within a shoe for providing optimum physical spacing, isolation, and cushioning of toes with respect to each other, moisture absorption from toe surfaces, and aeration of the toes, comprising a laterally extended continuous, non-interrupted base portion integrally provided with four generally similar, laterally spaced, upstanding, toe-separating and toe-spacing projection portions separated from each other by three intervening upwardly open toe-receiving recesses go with upper ends of each of said four toe-separating and toe-spacing projection portions being of upwardly convex, rounded configuration and being completely free and independent of each other, the plurality thereof being non-interconnected at their tops, and independently deflectable during use and defining each of said three intervening toe-receiving recesses in a manner completely upwardly open and downwardly engageable by a corresponding different toe through the complete open top end thereof, said laterally extended base portion being provided with an additional integral little toe extension portion at a first lateral extreme end thereof extending laterally beyond the corresponding adjacent, outwardly extreme one of said four laterally spaced, upstanding toe-separating and toe-spacing projection portions a distance slightly greater than the width of a little toe whereby to be adapted to fully underlie a little toe in a shoe; said laterally extended base portion being also provided with an additional integral big toe extension portion at a second lateral extreme end thereof and extending laterally beyond the corresponding adjacent, outwardly extreme one of said four laterally spaced, upstanding, toe-separating and toe-spacing projection portions a distance slightly greater than the width of a big toe whereby to be adapted to fully underlie a big toe in a shoe; said laterally extended base portion, said four laterally spaced, upstanding toe-separating and toe-spacing projection portions, said integral little toe extension portion, and said, integral big toe extension portion at opposite ends of said laterally extended base portion all being made of a readily compressible and collapsible, porous foam elastomeric material of a communicating cell type having a plurality of interconnecting air cells in air flow communication with exterior surfaces thereof and communicatingly dispersed and disseminated throughout the interior thereof whereby to provide a plurality of air flow and air circulation aeration passages extending completely therethrough.

Warren, Jr., et al., U.S. Pat. No. 5,653,128 describes a self-supporting sock providing for improved blood circulation in the leg of the user, the sock being formed by knitted fabric, the sock being of a height to extend below the knee of the user and having an elastic band at the top having elastic threads therein, the elastic band having a notch formed therein extending in a direction towards the sock heel portion, the notch being substantially the full length of the elastic band.

The prior art teaches the immobilization and clamping of the toes of the feet of a primate, but does not teach the application of opposing rigid clamping blocks with means for engaging a compressive wrap. The present invention fulfills these needs and provides further related advantages as described in the following summary.

SUMMARY OF THE INVENTION

The present invention teaches certain benefits in construction and use which give rise to the objectives described below.

The invention provides a pair of rigid clamping blocks, each with a length approximating the width of a human foot across the toes wherein one side of each of the blocks engages a compressible pad, and the other side of the blocks provides a longitudinal groove in an outfacing surface. A clamping wrap engages the longitudinal grooves in the pair of blocks when the blocks are placed on opposing sides of the toes and the clamping wrap encircles them, for applying a compressive force to the blocks and the toes sandwiched therebetween.

A primary objective of the present invention is to provide an apparatus and method of use of such apparatus that provides advantages not taught by the prior art.

Another objective is to provide such an invention capable of applying a compressive force to the toes of a human foot.

A further objective is to provide such an invention capable of selective compressive force.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings.

DETAILED DESCRIPTION OF THE INVENTION

The above described drawing figures illustrate the invention in at least one of its preferred embodiments, which is further defined in detail in the following description.

Figure 1:
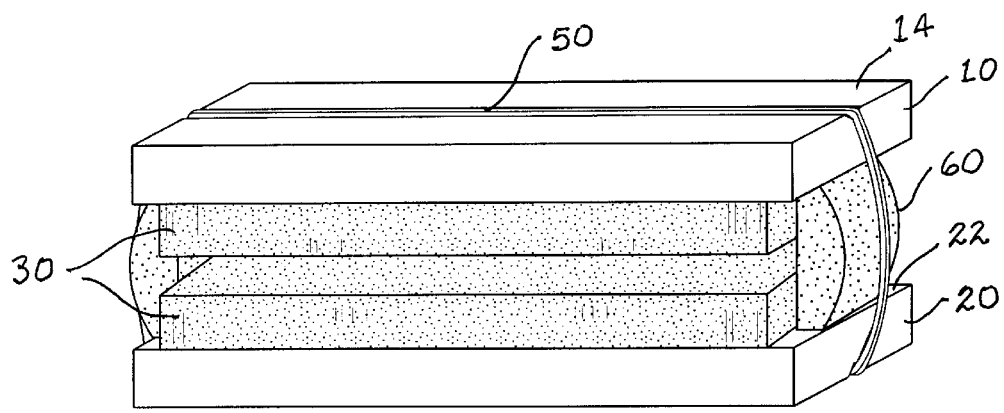
FIG. 1 is a perspective view of the preferred embodiment of the invention.
Figure 2:
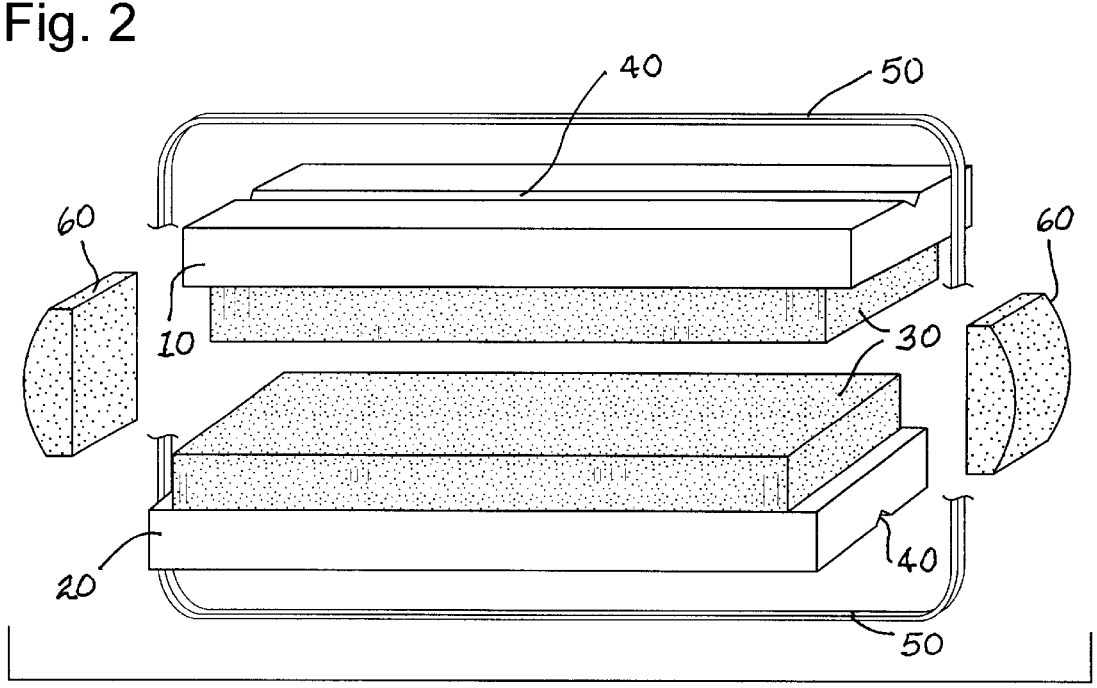
FIG. 2 is an exploded view thereof.
Figure 3:
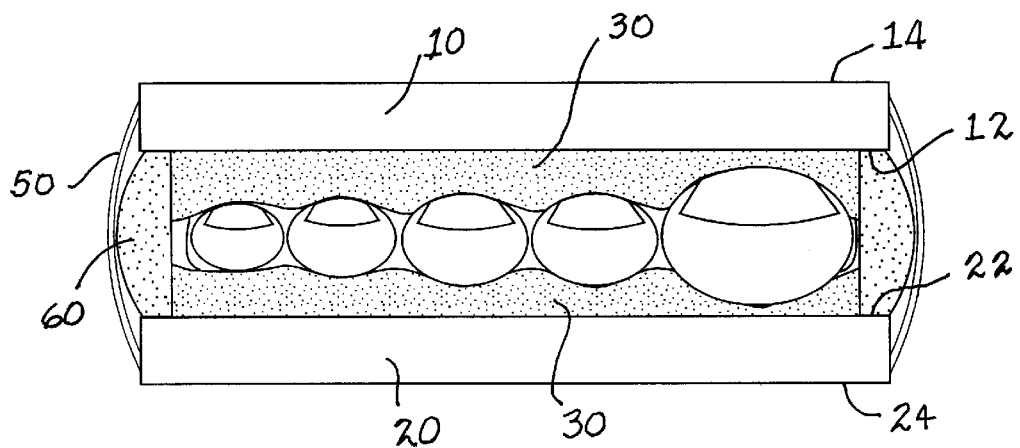
FIG. 3 is a front elevational view thereof showing a work piece.
Figure 4:
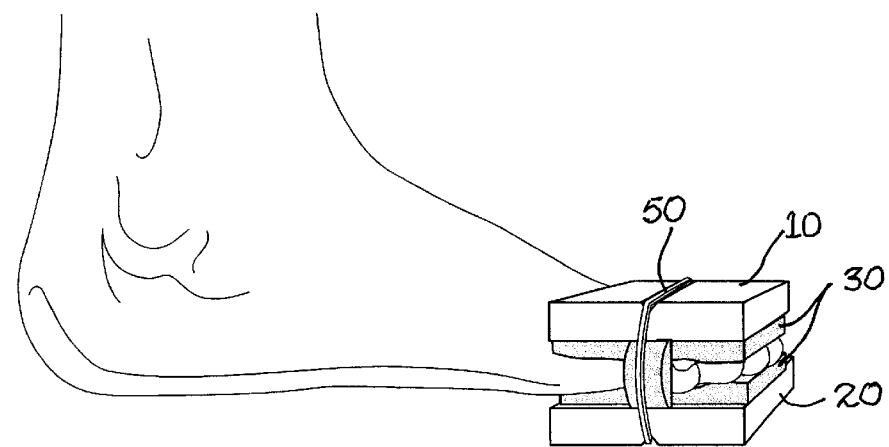
FIG. 4 is a perspective view of thereof.

The present invention is an apparatus having a pair of rigid clamping blocks 10, 20 are made of wood or plastic, for instance, where each of the blocks is of a length approximating the width of a human foot across the toes as shown in FIG. 3. One side 12, 22, of each of the blocks 10, 20 engages a compressible pad 30 of a rubber or other compressible substance, preferably by adhesive bonding of the pad 30 to the block 10 and 20. The other side 14, 24 of the blocks 10, 20 each provide a longitudinal groove 40 in a surface. A clamping wrap 50 is adapted by its size and flexibility for engaging the longitudinal grooves 40 in the blocks 10, 20 when the blocks are placed on opposing sides of the toes, as shown in FIG. 3, and the clamping wrap 40 encircles them. In this manner, a selective compressive force is applied to the blocks 10, 20 and, therefore, to toes sandwiched between them. The groove 40 is critical to the successful application of the invention as it holds the wrap 50 in place on the blocks and provides a unitizing force to the assembly. The entire assembly and each of its parts contribute to a novel holding and clamping structure which allows the toes to move slightly and to find their own position within the clamp, but also allows the toes to be straightened.

Preferably, the clamping wrap 50 is a continuous rubber band, a cord tied about the blocks and knotted, or a bandage such as adhesive tape. The groove 40 may be made as wide and deep as necessary to accept the selected clamping wraps of various sizes and elastic compliance.

Preferably, a pair of compressible side pads 60 of a rubber or similar material are positioned laterally to the blocks 10, 20 and the toes, as shown in FIG. 3. The side pads 60 are positioned within the clamping wrap 50 which holds them in place.

The method of the present invention provides for clamping the toes of a foot and includes placing the rigid clamping blocks 10, 20 on top and on bottom of the toes as shown in FIG. 3, placing a compressible pad 30 between each of the clamping blocks and the toes so as to cushion the toes, and then placing the clamping wrap 50 in the longitudinal grooves 40 in the clamping blocks so as to encircle the blocks and the toes to apply a compressive force to the toes. A pair of compressible side pads 60 are placed laterally to the blocks 10, 20 and the toes within the clamping wrap 50 to apply a side pressure so as to urge the toes away from a lateral tendency. In this method, the invention is applied to the toes for periods of time necessary to apply toe straightening forces to the toes, and are then removed intermittently to allow the toes to relax.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. An apparatus comprising in combination: a pair of rigid clamping blocks, each of the blocks of a length approximating the width of a human foot across the toes thereof; one side of each of the blocks engaging a compressible pad, the other side of the blocks providing a longitudinal groove in a surface thereof; and a clamping wrap adapted for engaging the longitudinal grooves in the pair of blocks when the blocks are placed on opposing sides of the toes and the clamping wrap encircles them, for applying a compressive force to the blocks and the toes sandwiched therebetween, the apparatus further comprising a pair of separable compressible side pads positioned laterally to the toes and in contact with the compressible pads and the pair of blocks, the side pads positioned within the clamping wrap for exerting a side force on the toes adjacent thereto.

2. The apparatus of claim 1 wherein the clamping wrap is a continuous rubber band.

3. The apparatus of claim 1 wherein the clamping wrap is a cord tied about the blocks and knotted.

4. The apparatus of claim 1 wherein the clamping wrap is a bandage.

5. A method of clamping the toes of a foot comprising the steps of: placing a pair of rigid clamping blocks on top and on bottom of the toes; placing a compressible pad between each of the clamping blocks and the toes, placing a clamping wrap in a longitudinal groove in the clamping blocks to encircle the blocks and the toes so as to apply a compressive force to the toes, and placing a pair of separable compressible side pads lateral to the toes in contact with the compressible pads and the pair of blocks, the side pads positioned within the clamping wrap for exerting a side force on the toes adjacent thereto.

* * * * *